(12) United States Patent
Atanasov (10) Patent No.: US 6,879,744 B2
(45) Date of Patent: Apr. 12, 2005

(54) OPTICAL MONITORING OF THIN FILM DEPOSITION

(76) Inventor: Georgi A. Atanasov, 6911 Western Ave., NW., Washington, DC (US) 20015

(*) Notice: Subject to any disclaimer, the term of this patent is extended or adjusted under 35 U.S.C. 154(b) by 0 days.

(21) Appl. No.: 10/627,680

(22) Filed: Jul. 28, 2003

(65) Prior Publication Data

US 2004/0131300 A1 Jul. 8, 2004

Related U.S. Application Data

(60) Provisional application No. 60/438,174, filed on Jan. 7, 2003.

(51) Int. Cl.[7] .............................. G02B 6/26; G02B 6/42
(52) U.S. Cl. .............................. 385/15; 356/630; 438/9
(58) Field of Search .............................. 385/37, 24, 16, 385/14, 31; 156/345, 643; 356/445, 630, 382; 204/192.26; 427/10; 359/883, 72

(56) References Cited

U.S. PATENT DOCUMENTS

| | | | | |
|---|---|---|---|---|
| 3,824,017 A | * | 7/1974 | Galyon | 356/504 |
| 4,140,078 A | * | 2/1979 | Wilmanns | 118/665 |
| 4,311,725 A | * | 1/1982 | Holland | 427/10 |
| 4,855,013 A | * | 8/1989 | Ohta et al. | 117/85 |
| 4,888,199 A | * | 12/1989 | Felts et al. | 427/10 |
| 5,000,575 A | * | 3/1991 | Southwell et al. | 356/632 |
| 5,002,631 A | * | 3/1991 | Giapis et al. | 216/60 |
| 5,153,669 A | * | 10/1992 | DeGroot | 356/489 |
| 5,241,366 A | * | 8/1993 | Bevis et al. | 356/632 |
| 5,425,964 A | * | 6/1995 | Southwell et al. | 427/10 |
| 5,523,882 A | * | 6/1996 | Rahmlow | 359/580 |
| 5,684,574 A | * | 11/1997 | Shiokawa et al. | 356/72 |
| 5,880,823 A | * | 3/1999 | Lu | 356/72 |
| 5,923,429 A | * | 7/1999 | Takeuchi et al. | 356/632 |
| 6,039,806 A | * | 3/2000 | Zhou et al. | 118/665 |
| 6,110,337 A | * | 8/2000 | Sullivan et al. | 204/298.26 |
| 6,129,807 A | * | 10/2000 | Grimbergen et al. | 156/345.24 |
| 6,278,809 B1 | * | 8/2001 | Johnson et al. | 385/12 |
| 6,338,775 B1 | * | 1/2002 | Chen | 204/192.11 |
| 6,381,021 B1 | * | 4/2002 | Somekh et al. | 356/445 |
| 2002/0075486 A1 | * | 6/2002 | Zhang et al. | 356/630 |
| 2002/0108848 A1 | * | 8/2002 | Miyamura et al. | 204/192.26 |
| 2004/0008435 A1 | * | 1/2004 | Takahashi et al. | 359/883 |

* cited by examiner

Primary Examiner—Brian Healy
Assistant Examiner—Ryan Lepisto
(74) Attorney, Agent, or Firm—Womble Carlyle (57) ABSTRACT

An optical monitoring system for monitoring thin film deposition on a substrate includes a support bridge that is attached on an inside of a deposition chamber. The system further includes a fiber optic collimator having an optical fiber for incoming light, and another fiber optic collimator having an optical fiber for transmitted or reflected light from the substrate. The system further includes a shutter that is closed when a desired thin film thickness is deposited on the substrate.

58 Claims, 10 Drawing Sheets

OPTICAL MONITORING OF THIN FILM DEPOSITION

RELATED APPLICATIONS

This application claims the benefit of U.S. Provisional Application No. 60/438,174, filed Jan. 7, 2003.

FIELD OF THE INVENTION

One embodiment of the present invention is directed to thin film deposition on a substrate. More particularly, one embodiment of the present invention is directed to optical monitoring of thin film deposition on a substrate.

BACKGROUND INFORMATION

There is a growing demand for precision optics instruments based on optical thin films, particularly for telecommunication, surveillance, astrophysics, laser and printing technology, medical instrumentation. etc. This has resulted in a growing need of precise in-situ optical monitoring of the growing thin films in the process of deposition. The new generation of precision optical coatings require in-situ determination of a number of physical and optical properties of the deposited layers, such as optical thickness, complex index of refraction of the deposited layer and the thin film stack as a whole, inhomogeneity, absorption, scattering, etc.

Known in-situ optical monitoring systems typically operate by monitoring the light interference through the coated substrate or a special sample substrate (referred to as a "witness"), and by calculating the needed optical parameters of the system "substrate coating", or by monitoring the polarized components of the light coming from the substrate and calculating its ellipsometric parameters. The known systems may monitor the transmitted light, the reflected light, or both.

In all known systems, however, the monitoring beam enters the deposition chamber through a transparent window mounted on the chamber walls, and leaves the chamber through another window in the case of transmission monitoring, or through the same or another window in the case of reflection monitoring. The needed clear path for the optical beam running through the chamber has to be provided for when the deposition chamber is designed. In some cases, a system of mirrors or beam splitters is used to direct the monitoring beam to the monitored sample or to take a power reference of the monitored light. In some other cases, a system of polarization components is also used to make ellipsometric measurements.

Figure 1:
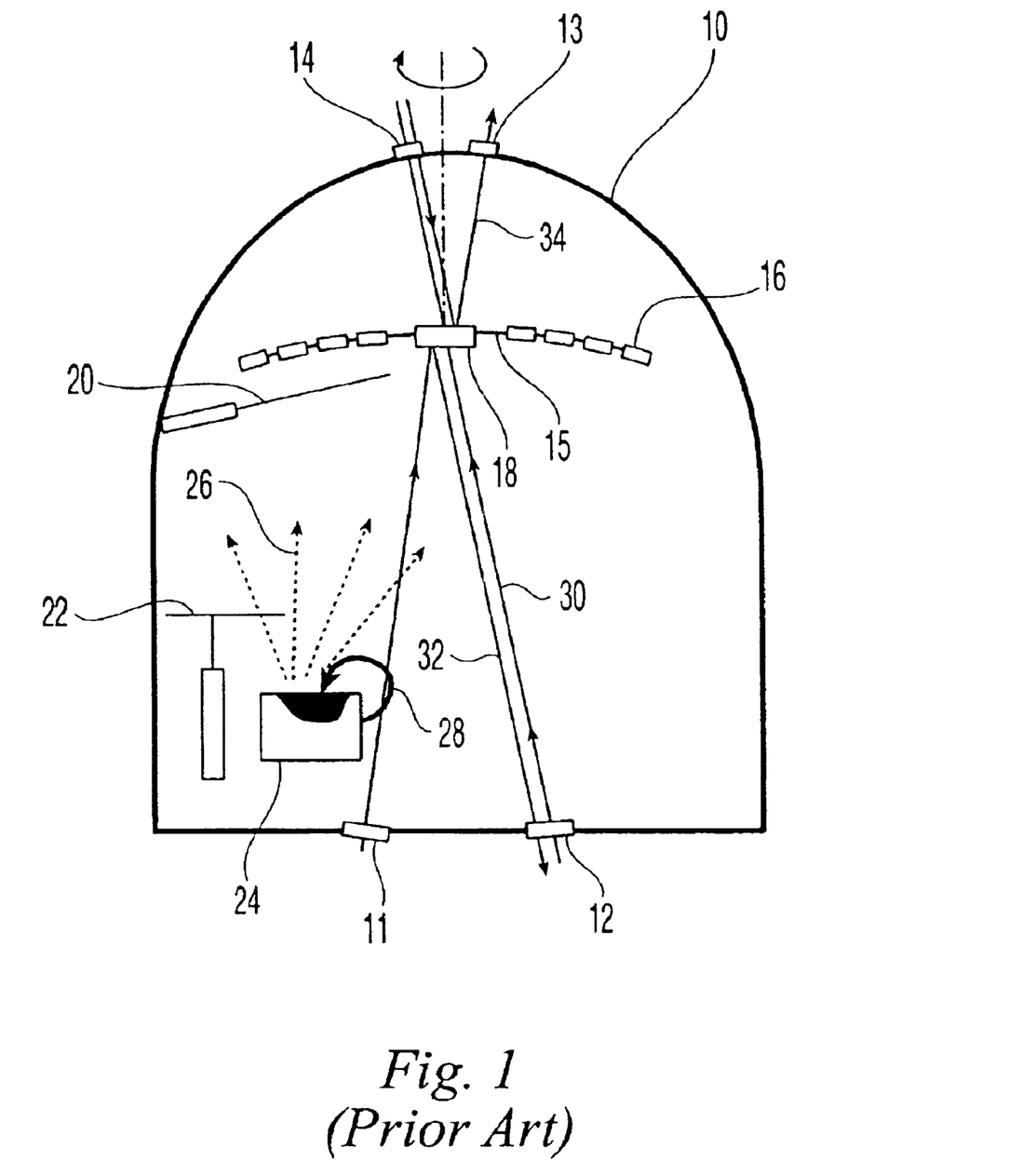
FIG. 1 is a sectional view of a prior art vacuum deposition chamber having optical monitoring of a thin film deposition on a substrate.

FIG. 1 is a sectional view of a prior art vacuum deposition chamber 10 having optical monitoring of a thin film deposition on a substrate. Vacuum deposition chamber 10 includes optical windows 11–14, and a dome substrate holder 15 for holding substrates 16 and a monitoring sample 18 (or witness 18). A mask 20 provides the needed uniformity of the coating over all of substrates 16. Chamber 10 further includes a mechanical shutter 22 that closes a vapor source 24 and prevents vapors 26 generated by an electron beam 28 to reach substrate 16 as the optical thickness on monitoring sample 18 is reached. The monitoring can be performed in transmission 30, in reflection 32 from the coated side of the sample 18 or in reflection 34 from the uncoated side of sample 18.

The optical monitoring of chamber 10 is performed on witness 18, which may be monitored constantly during the whole deposition process or may be changed a few times during the process. Witness 18 is placed approximately at the center of the rotation of substrate holder 15. Substrate holder 15 typically has a dome shape, but shapes such as plane, cylindrical or others are also possible. Planetary rotation of the substrates is also often used.

With a specially designed mask, the optical monitoring of witness 18 performed at one or several wavelengths can ensure that the right optical thickness of the layers is deposited on the samples positioned on a dome and performing one or more independent rotations with respect to the center of the dome. When the desired optical thickness of the layer is reached on witness 18, vapor source 24 closes automatically by shadowing the vapors with mechanical shutter 22. Typically the monitoring light beam is modulated at some frequency and lock-in amplifiers are used to detect the modulation frequency. The intensity of the passing through the witness light is measured at a certain wavelength. In some cases the incident light beam is split on two—one monitoring beam and one reference beam. Further, in other cases during one modulation cycle the same beam passes a first phase when it goes for monitoring of the substrate, a second phase when it goes for reference and a third "dark" phase.

Figure 2:
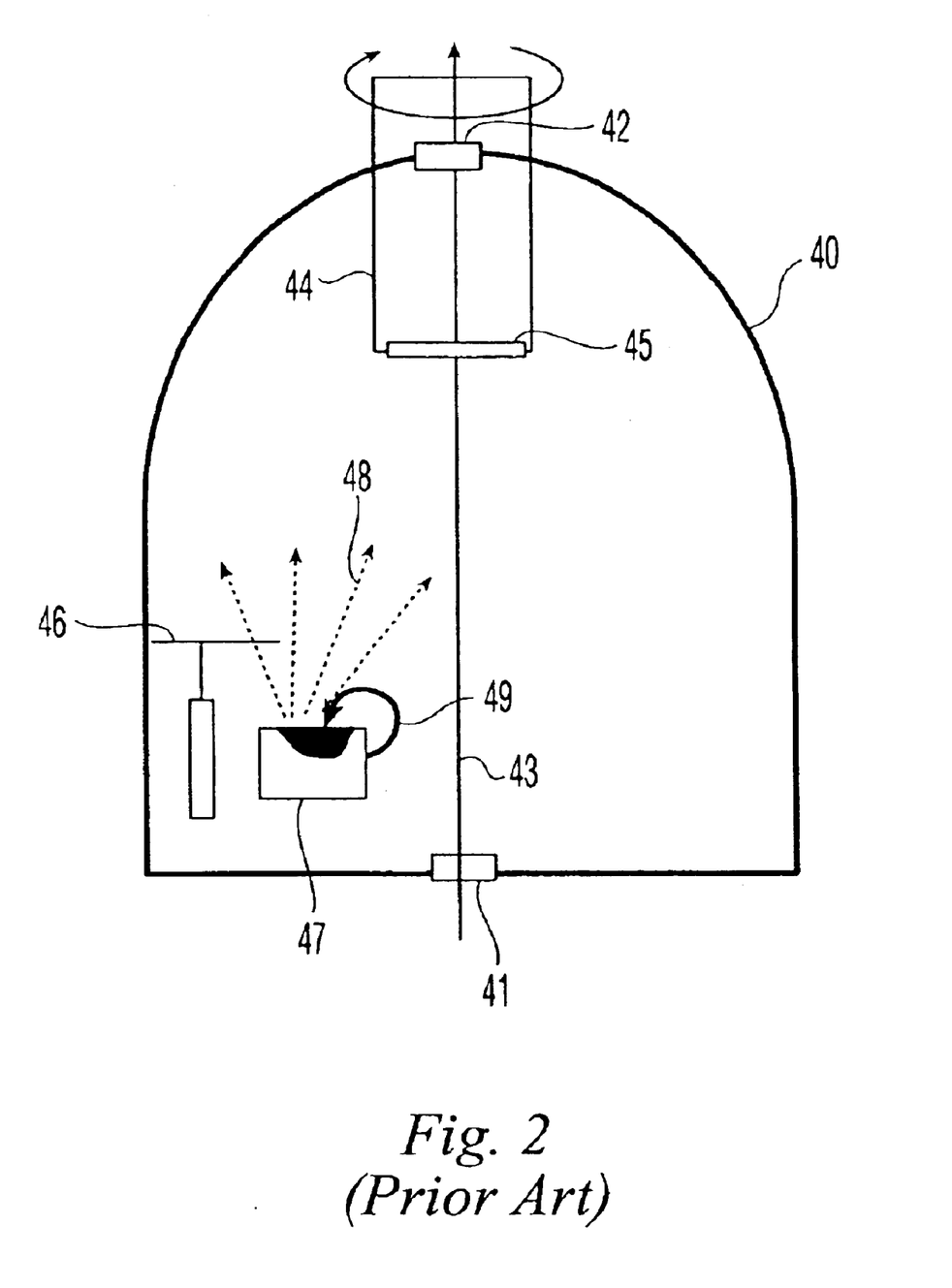
FIG. 2 is a sectional view of another prior art vacuum deposition chamber having optical monitoring of a thin film deposition on a substrate.

FIG. 2 is a sectional view of another prior art vacuum deposition chamber 40 having optical monitoring of a thin film deposition on a substrate. Chamber 40 has optical windows 41, 42 for monitoring beam 43, and a rotational substrate holder 44 with a substrate 45. A mechanical shutter 46 closes the vapor source 47 and prevents the vapors 48 generated by the electron beam 49 from reaching substrate 45 as the optical thickness on the coating is reached. Monitoring beam 43 operates in transmission.

In chamber 40, the optical monitoring is performed in transmission directly through the center or slightly off-center of the rotational substrate. The optical beam entering the chamber is first modulated with a certain frequency and focused on the monitored substrate. After passing through the substrate the beam is re-focused on the entrance slit of the monochromator and then the beam with a selected wavelength goes to the detector. In order to transport the light beam outside the chamber very often different optical fiber bundles are used. When the desired optical thickness of the layer is reached on the substrate, the vapor source closes automatically by the shutter. This arrangement allows direct monitoring of the deposited coating without need for a mask.

Figure 3:
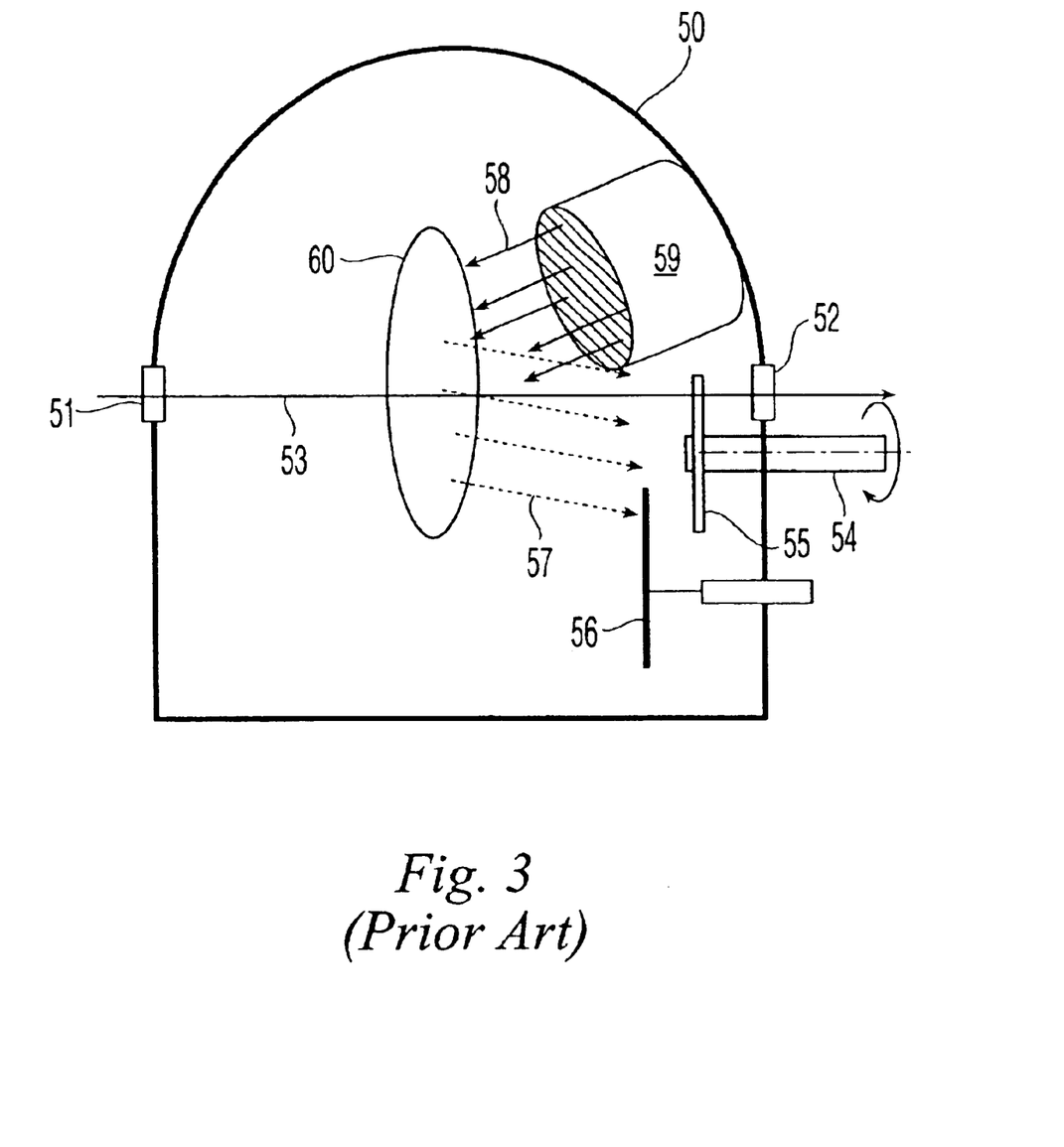
FIG. 3 is a sectional view of another prior art vacuum deposition chamber having optical monitoring of a thin film deposition on a substrate.

FIG. 3 is a sectional view of another prior art vacuum deposition chamber 50 having optical monitoring of a thin film deposition on a substrate. Vacuum deposition chamber 50 has optical windows 51, 52 for monitoring a beam 53, and a rotational substrate holder 54 with a substrate 55. A mechanical shutter 56 closes substrate 55 and prevents the sputtered particles 57, generated as a sputtering ion beam 58 from a sputtering ion source 59 and which sputters a target 60, to reach substrate 55 as the optical thickness on the coating is reached. Monitoring beam 53 operates in transmission.

In prior art chamber 50, the optical monitoring is performed in transmission slightly off-center of the rotational substrate through the windows mounted on the chamber walls. The deposition particles are sputtered from a target by means of sputtering source. When the desired optical thickness of the layer is reached on the substrate the shutter is closed automatically in front of the substrate. As with chamber 40 of FIG. 2, this allows direct monitoring of the deposited coating without the need of a mask, even though a mask can also be used. The monitoring is performed either during the full rotation cycle of the substrate or during a part of it.

In general, known optical monitoring systems have several significant drawbacks. They typically allow only one monitoring system per deposition chamber. This does not allow multiple optical monitoring systems to be used in the same chamber in order to monitor more than one or all deposited substrates at the same time. In addition, known optical monitoring systems cannot deposit optical coatings with different designs on different substrates at the same time. This results in inefficient use of the chamber space, the electrical power, the coated material and the deposition time.

Further, in known systems where the monitoring is performed through the deposited substrate there is only one deposited substrate at a time. No multiple substrate deposition is possible. In addition, all known systems have a deposition source mechanical shutter which automatically shuts the vapor source and stops the deposition on all the substrates at the same time. None of the systems allow for each substrate to have its own autonomous shutter.

Further, known monitoring systems are designed to fit a certain chamber geometry and cannot be used for other geometries without significant redesign, which is not always possible and is expensive. The chamber design includes the optical monitoring system installation. If the chamber is designed not to have optical monitoring system (as 80% of all the deposition chambers are) it is very difficult to retrofit an optical monitoring system unless significant hardware work is performed.

Further, none of the known systems are portable and designed to fit all chamber geometries. Most existing chambers, including old chamber models, are not designed to have optical monitoring system. These chambers have limited use and do not allow deposition of complex optical coatings and filters because of the lack of monitoring.

Based on the foregoing, there is a need for an optical monitoring system that is portable and adaptable to current chambers, and can monitor multiple substrates simultaneously.

DETAILED DESCRIPTION

One embodiment of the present invention is an optical monitoring system that is portable so that it easy to install into existing vacuum chambers having different geometries, and so that multiple monitors can be installed in the same chamber. Embodiments of the present invention also include an autonomous mechanical shutter that allows different areas of the same substrate to be monitored separately during the same deposition process.

Figure 4:
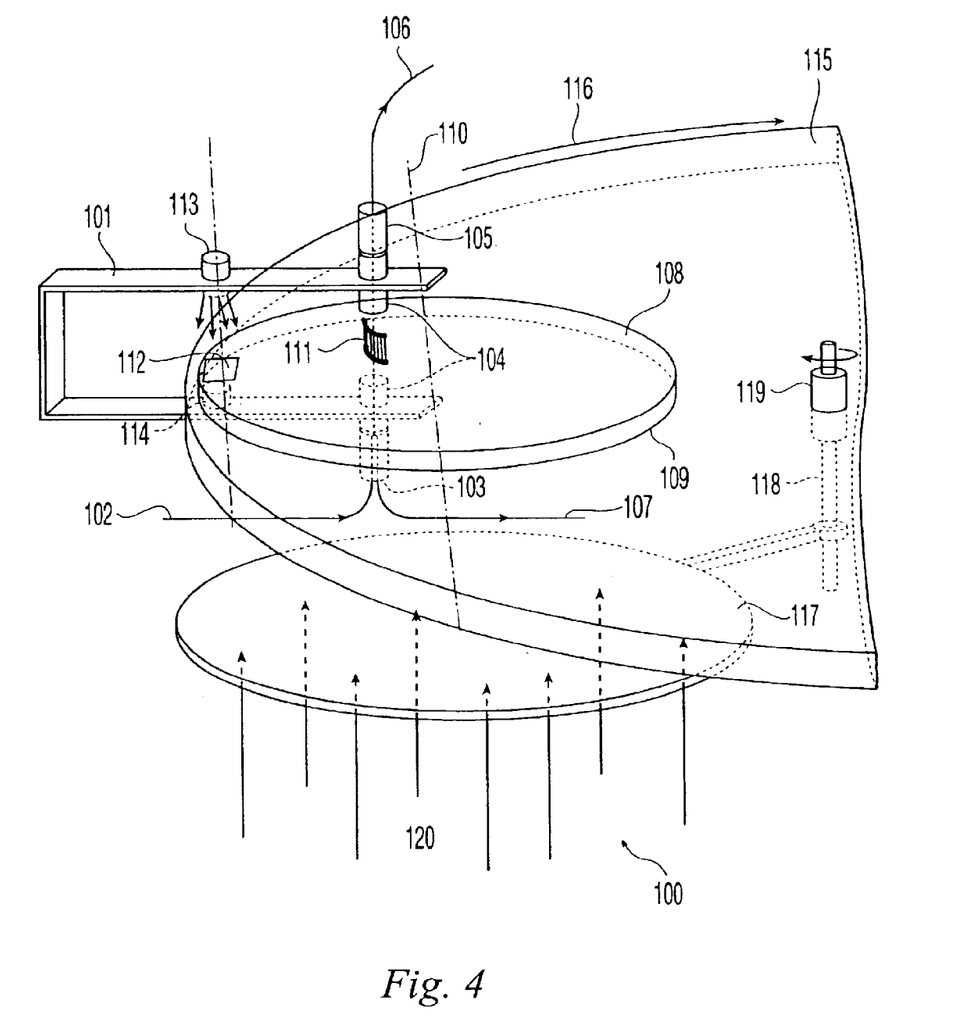
FIG. 4 is a perspective view of an optical monitoring system in accordance with one embodiment of the present invention.

FIG. 4 is a perspective view of an optical monitoring system 100 in accordance with one embodiment of the present invention. System 100 includes a mechanical support bridge 101 that is designed to be installed on a deposition chamber wall inside the vacuum chamber. Support bridge 101 supports two fiber optics collimators that include a fiber 102 for incoming light, a two-fiber ferule 103, gradient index ("GRIN") lenses 104, a single-fiber ferule 105, a fiber for transmitted light 106 and fiber for reflected light 107.

A monitored substrate 108 having a coated side 109 and a geometrical axis 110 is monitored by the collimated light within a monitored area 111 each time area 111 passes through the collimators. Substrate 108 includes a mark 112 that generates a strobe signal as it blocks an optical beam from a light emitting diode 113 to a detector 114. Monitored substrate 108 is placed, likely with other substrates, on a large substrate holder 115 which rotates in direction 116. A mechanical shutter 117 having a rotation axis 118 closes substrate 108 from the incoming deposition material when the optical thickness on substrate 108 is reached. Shutter 117 is operated by a rotation driver 119 that is fixed on substrate holder 115. Shutter 117 has two available positions—an open position when the deposition takes place and close position when shutter 117 closes substrate 108 from the incoming deposition material 120.

Optical monitoring system 100 can be run in three separate modes: in transmission mode, in reflection mode and in transmission-reflection mode. Generally the transmission mode is preferable because the monitoring device is easier to align and harder to misalign during the deposition process. The reflection mode is preferable when dielectric or metal mirrors with high reflection are deposited. However, it is harder to align the collimators with respect to the substrate and is more sensitive to substrate wobbling during rotation. In the transmission-reflection mode the system monitors both the transmission and reflection of the coating-substrate, which can be very helpful for more precise cutting point determination of layers and for fabrication of coatings with high absorption, mirrors with high reflectivity or some complex optical coatings. The transmission and reflection functions monitored simultaneously provide better quality information for curve fitting and precise prediction of the turning points and swings of the deposited layers.

In another embodiment, the reflected from the coating light does not go to the fiber for reflected light 107, but couples back into the fiber for incoming light 102 and is further separated from the incoming light by an optical circulator or other beam splitting device.

Figure 5:
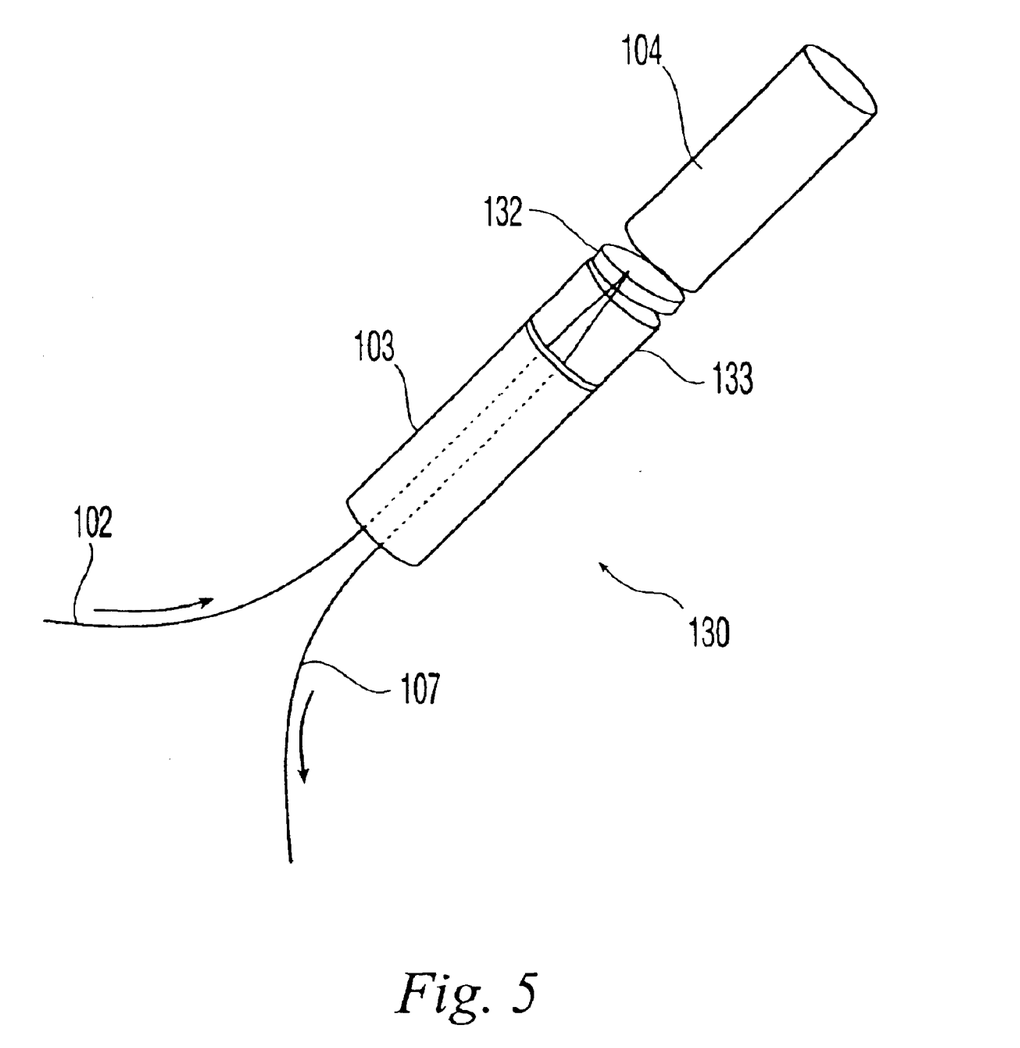
FIG. 5 is a perspective view of an incoming optical collimator for an optical monitoring system in accordance with another embodiment of the present invention.

FIG. 5 is a perspective view of an incoming optical collimator 130 for an optical monitoring system in accordance with another embodiment of the present invention. Incoming optical collimator 130 is the same as the incoming optical collimator of FIG. 4 except that a tap optical filter 132 and an alignment glass rod 133 are placed between the two-fiber ferule 103 and the GRIN lens 104. Tap filter 132 provides a reflected signal for power reference which couples into the fiber for reference light 107. It may represent a thin film filter designed to reflect 2–10% of the incoming light power. Glass rod 133 is used to create the needed offset between the incoming beam and the reflected from the tap beam so that the reflected from the tap beam couples exactly to the fiber for reference light 107 in ferule 103.

One embodiment of collimator 130 is used solely in transmission mode and the reflected beam from the monitored substrate is misaligned so that no light from the monitored substrate is coupled back into the fiber for reference light 107 to interfere with the reflected light from the tap. Other embodiments that can be used for getting a signal for power reference, such as fused biconical tapered couplers and leak-mode waveguides, can be used for all monitoring modes.

Figure 6:
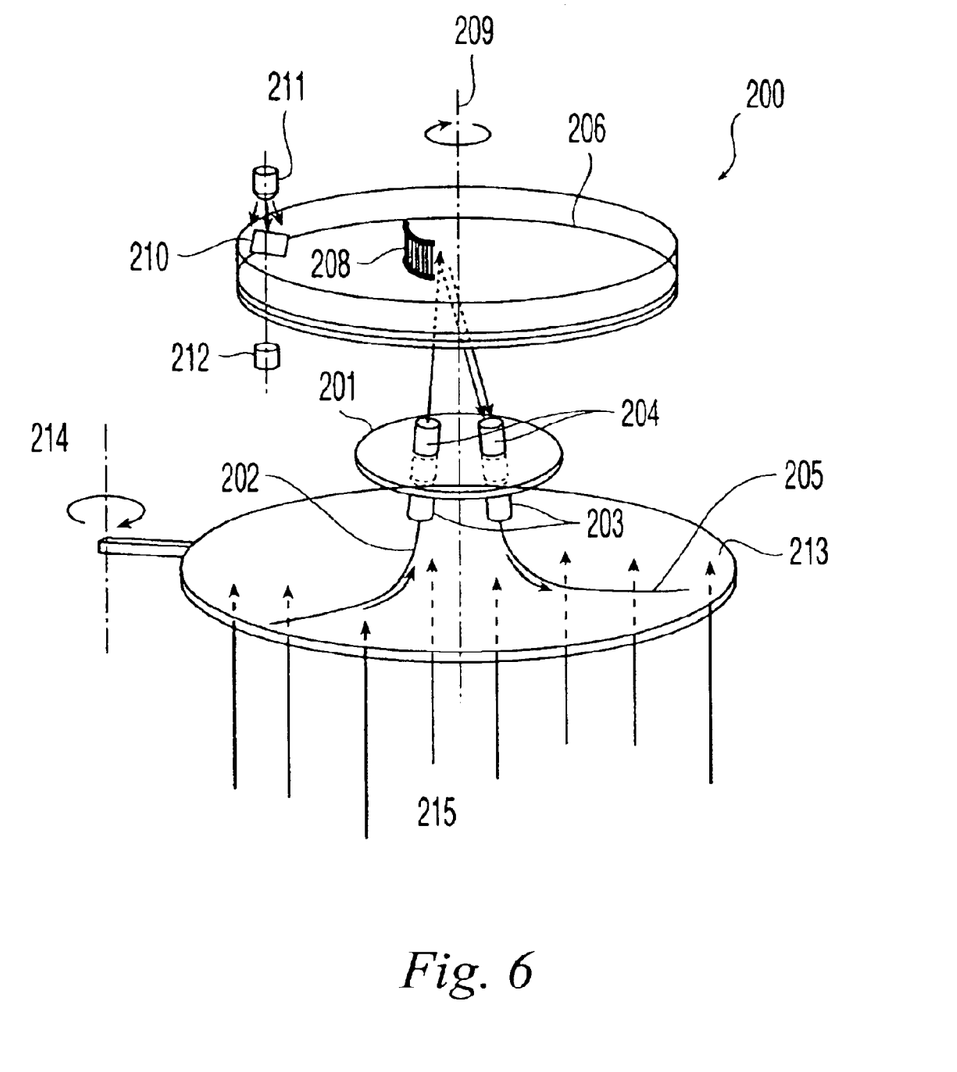
FIG. 6 is a perspective view of an optical monitoring system in accordance with another embodiment of the present invention.

FIG. 6 is a perspective view of an optical monitoring system 200 in accordance with another embodiment of the present invention. Monitoring system 200 includes a reflective collimator pair. A mechanical support 201 supports two fiber optics collimators that include a fiber 202 for incoming light, single-fiber ferules 203, GRIN lenses 204 and fiber 205 for reflected light. The monitored substrate 206 with its coated side rotates together with its substrate holder (not shown) in direction 209. The monitoring system monitors a substrate area 208. The substrate has a mark 210 for strobe signal generation as its blocks the optical beam from a light emitting diode 211 to a detector 212. A mechanical shutter 213 having a rotation axis 214 closes the substrate 206 from the incoming deposition material 215 as the optical thickness on the substrate is reached. Shutter 213 is fixed on the same substrate holder as the substrate and rotates together with the holder. The large substrate holder and the way the shutter is fixed on it and closes the substrate are the same as shown in FIG. 4.

Embodiments of monitor system 200 are designed to be used in reflection mode only. The incident angle of the monitoring beam can be designed to be exactly the angle at which the deposited coating is designed to operate. Monitor system 200 is ideally used when coatings operating at angles different than normal incidence or certain polarization coatings are manufactured, such as with the production of very large metal mirrors or very thick substrates as well as substrates with complex curvatures.

Figure 7:
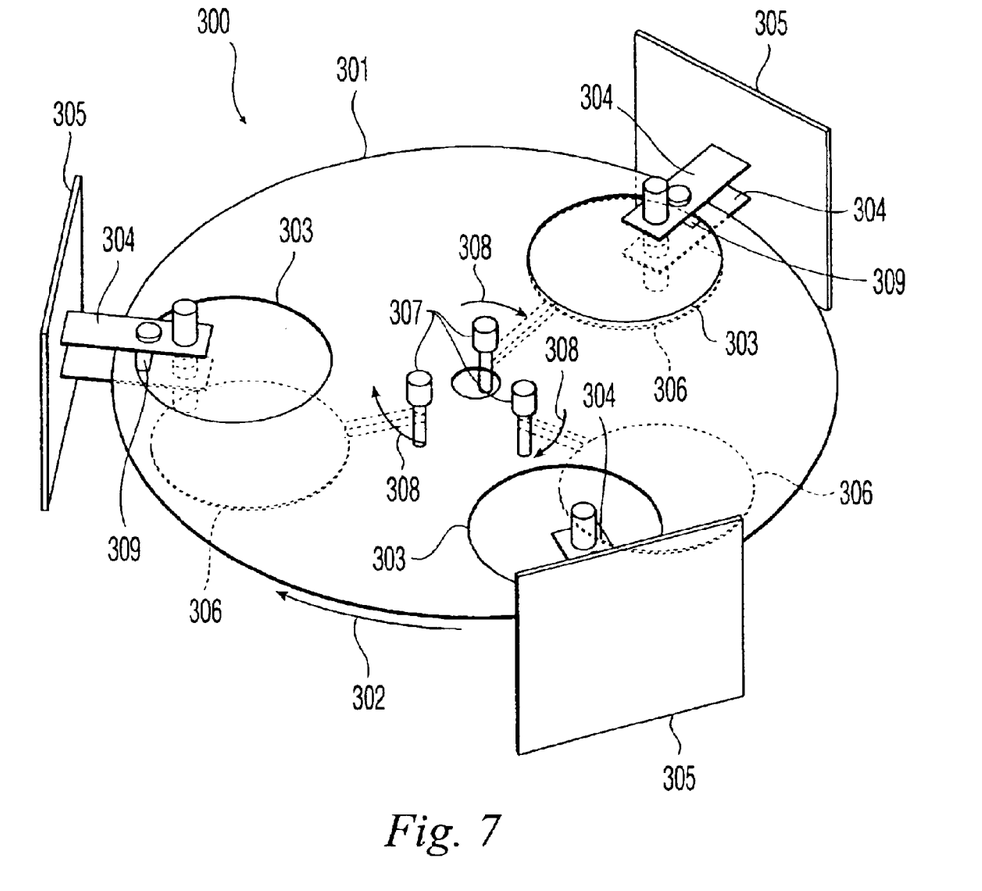
FIG. 7 is a perspective view of an optical monitoring system in accordance with another embodiment of the present invention.

FIG. 7 is a perspective view of an optical monitoring system 300 in accordance with another embodiment of the present invention. Monitoring system 300 includes a planar substrate holder 301 with direction of rotation 302 holding three separate substrates 303, each one monitored by its own monitoring device 304. The monitoring devices are firmly fixed on the deposition chamber walls 305 and do not rotate or move during the monitoring process. Three shutters 306 with their rotation drivers 307 rotate to their closed positions in direction 308. Each of them is autonomously controlled and designated to shut its designated substrate only. Shutters 306 are mounted on substrate holder 301 and lay below substrates 303 and monitoring devices 304. One of shutters 306 is shown in a closed position to illustrate the fact that when closed, the shutter also covers the substrate and the monitoring device. For illustration, strobe pulse generation 309 marks are placed on the back side of the substrate.

Figure 8:
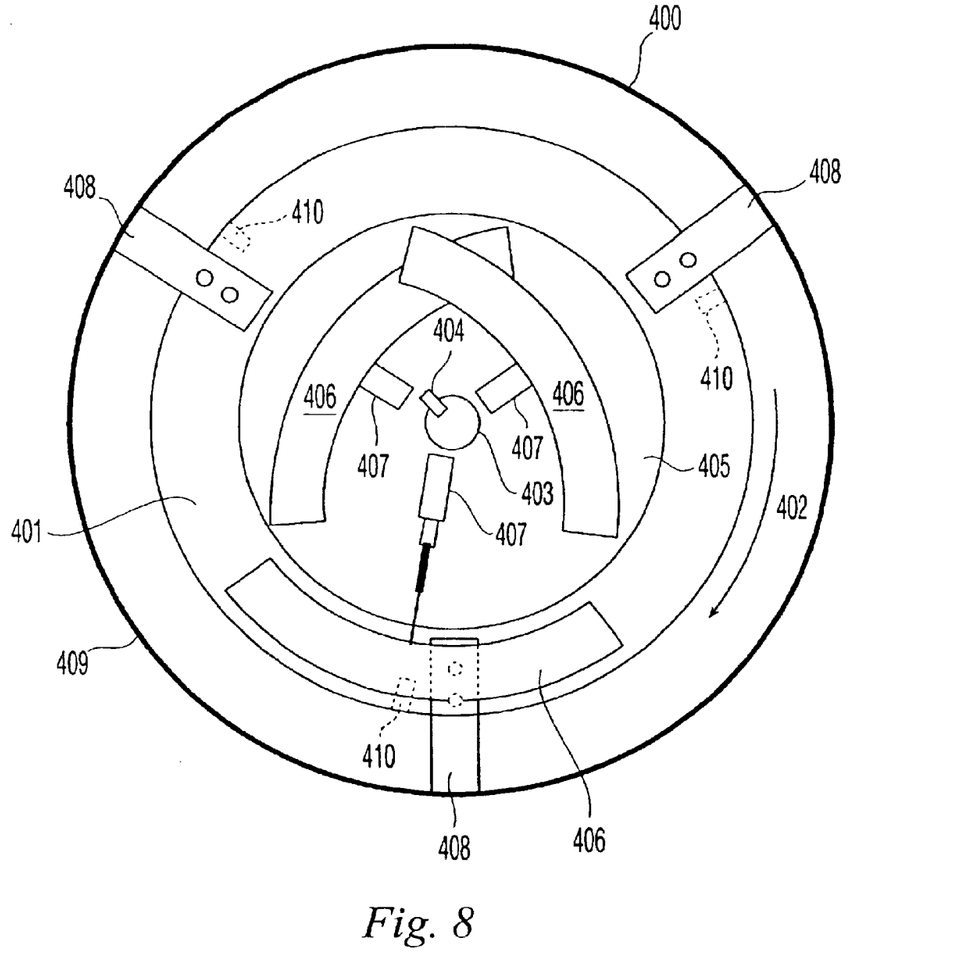
FIG. 8 is a top view of an optical monitoring system in accordance with another embodiment of the present invention.

FIG. 8 is a top view of an optical monitoring system 400 in accordance with another embodiment of the present invention. Monitoring system 400 allows for in-situ optical monitoring of three separate areas on the same large substrate, which rotates around its center. A large glass substrate 401 (shown from the coated side) with direction of rotation 402, fixed in the center to a substrate holder 403 having a mark 404 for designation of the starting position has a central area covered by a metal shield 405 which covers some undesired for deposition substrate area. Three shutters 406 are also fixed on a metal shield 405 through three fixtures 407 with telescopic drivers allowing them to pop up and close the designated area of the substrate. As the shutters pop up and close the designated substrate area, they cover both the substrate and the monitoring device, as it is shown with one of the shutters for illustration. Shield 405 rotates together with the shutters and the glass substrate around the same axis. Three monitoring devices 408 are fixed on a metal ring 409. Monitoring devices 408 are numbered with respect to the substrate starting position and mark 404. Substrate 401 during its rotation slides between the collimators of monitoring devices 408, allowing the monitoring process to be performed. Strobe generation marks 410 are put on the back side of substrate 401 and each generates the strobe signals each for its own monitoring device as they are numbered with respect to mark 404 in the same way as the monitoring devices are numbered.

The embodiment of FIG. 8 is preferable when a large substrate is deposited and diced into small pieces, as is the case with DWDM coatings. It can be used to deposit filters at few center wavelengths at the same time, cutting the needed deposition time by ⅔.

The monitoring light source in embodiments of the present invention could be any light source in UV, visible and infrared region such as deuterium or mercury light source, tunable of fixed-wavelength laser, broadband ASE source or any white light source. When a broadband or white light source is used, after passing through or reflected from the substrate, the monitoring beam subsequently passes through a spectral dispersive or wavelength selective component such as monochromator, diffraction grating, spectral analyzer or optical filter. After passing through the dispersive device and being wavelength selected, the light signal goes to the receiver. The signal from the receiver undergoes an analog-digital conversion and continues for further signal processing.

In operation, an embodiment of the optical monitoring systems such as shown in FIG. 4 is installed on the chamber wall inside the vacuum chamber in the vicinity of the rotation substrate or substrate holder, aligned toward the monitored substrate or specimen as it passes around it during rotation, and fixed. During its rotation around its axis or as a part mounted on a larger substrate holder together with other substrates, the monitored substrate passes through the aligned position or positions allowing the monitor system to perform the monitoring process. The monitored substrate can rotate around its own geometrical axis, be a part of rotation around another axis (usually a large substrate holder) or rotate around more than one axis as is the case with planetary motions. In all cases the monitored substrate/substrates or areas of the same substrate come to the aligned position during the rotation.

In other embodiments, the deposited substrate may not rotate at all and stay in the same position during the whole deposition process. In some embodiments, it is possible and advisable even to perform the monitoring function from the back side of the substrate which avoids the shadowing of the deposited substrate by the monitoring device. In other embodiments, a portion of the monitor system such as collimator 104 is directly attached to the substrate, such as by glue.

During one rotation of the substrate or the substrates, the monitor system receives analog data for the transmission at the chosen wavelength within a complete monitoring ring. However, after the reception, the analog signal undergoes an analog-digital conversion with a chosen sampling rate as if the monitored ring were divided on a number of monitored points.

In one embodiment of the present invention, the optical thickness of the deposited layer is calculated not by using all the digital points within one ring, but only a certain number of them, which cover a monitoring area (part of the ring) that is predetermined by the operator.

As an example, if the rotation speed is 60 rpm (one rotation cycle is 1 s), and the sampling rate is 50 KHz, after the digital conversion there will be 50,000 digital points (numerical transmission values) within one monitoring ring. The computer averages the transmission values of a small portion of the 50,000 values, for example only the first 250 points of the rotation cycle. If the monitoring ring has a radius of 25 cm, 250 monitoring points will cover an area with a length of 0.785 cm. Such an area is scanned during a time duration (monitoring pulse) of $\frac{1}{200}$ s=5 ms.

For the purposes of this patent, "monitoring pulse" refers to the duration of such a pulse during which the chosen number of substrate points is scanned during one rotation cycle of the substrate or the substrate holder. Monitoring pulse is related to A-D conversion. In one embodiment, the monitoring process comprises one or more short monitoring pulses, generated each time the appropriate strobe mark crosses the aligned position. The duration of the monitoring pulse depends on the type and complexity of the deposited coating, the type and geometry of the substrate, the rotation speed of the substrate or the substrate holder, etc. It is a parameter determined by the operator of the optical monitor system, and is one of the initial input parameters. The area monitored during one monitoring pulse typically has the form of a part of a ring as shown in FIG. 4 and FIG. 5, but may also be more than one part of a ring, a complete ring or a single spot.

Complex multilayer coatings (such as DWDM coatings) require both bigger rotation speed and shorter monitoring pulse, while more simple coatings (such as broadband mirrors, etc.) allow reduction of the rotation speed and increase of the monitoring pulse duration, which is beneficial for better coating uniformity. For example, when the deposited coating is a complex narrow bandpass filter, the rotation speed can be increased to over 15 rps and the time for monitoring a complete ring becomes shorter than 67 ms. However, the complexity of the coating typically requires monitoring an area much smaller than a complete ring. In this case the operator may prefer to set the monitoring pulse duration to 1 ms or smaller. The size of the monitored area is also dependent on the distance at which the monitoring device is aligned from the center of rotation of the substrate. Therefore, the operator also inputs an additional variable of the radius of the monitored ring.

The algorithm for optical thickness calculation of the layers is usually based on calculation of the characteristic matrix or the transfer function of layered structure of the coating-substrate, which is known in the art. The input parameters are generally the indexes of the substrate and the coating materials, the wavelength of monitoring, the calculation of the turning points of the monitored periodic function, the prediction and determination of the cutting point for each layer and the generation of the needed coating's history database.

Figure 9A:
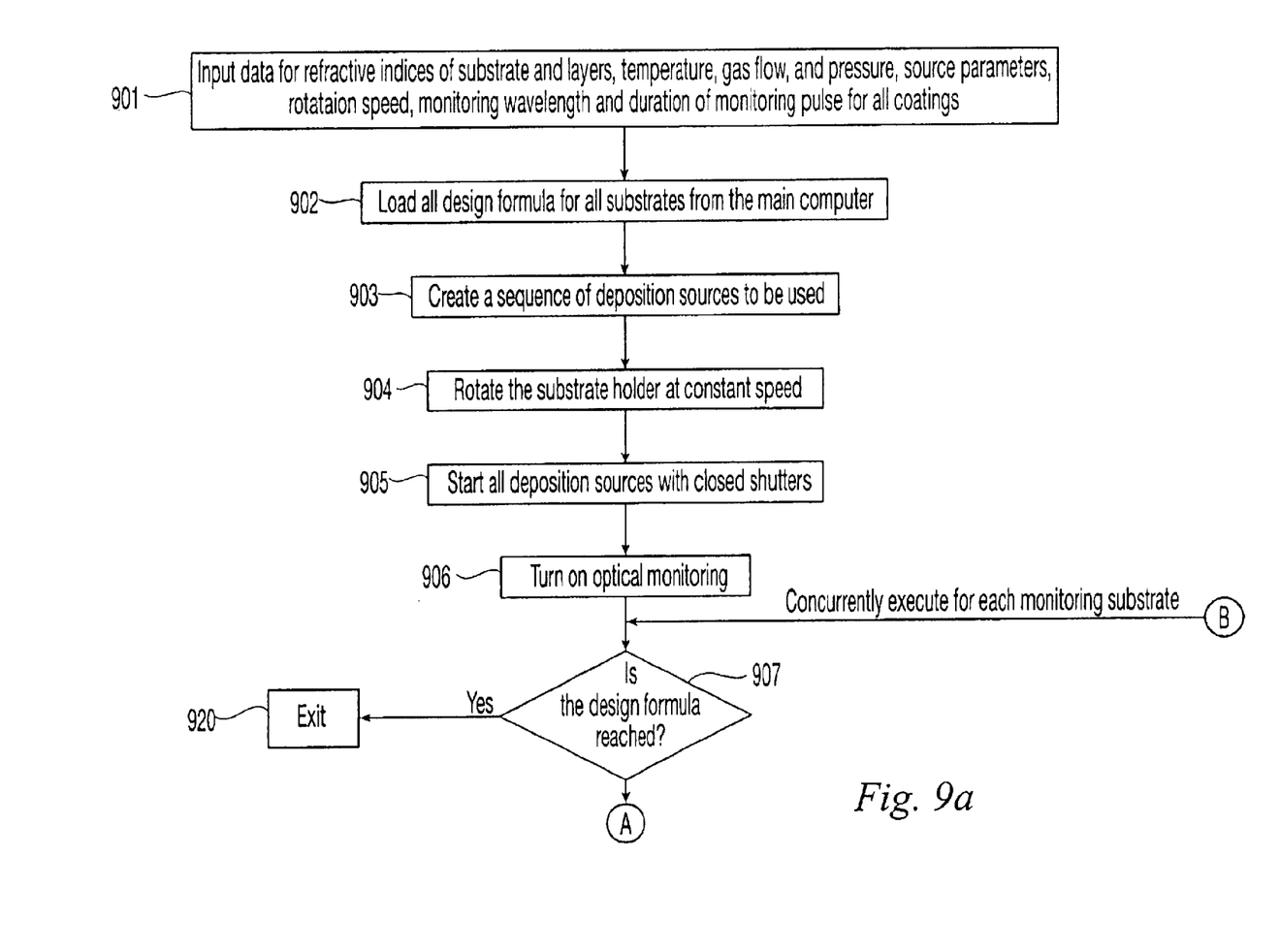
FIG. 9 is a flow diagram of the functionality performed by an optical monitoring system in accordance with one embodiment of the present invention when performing the deposition and in-situ monitoring process.
Figure 9B:
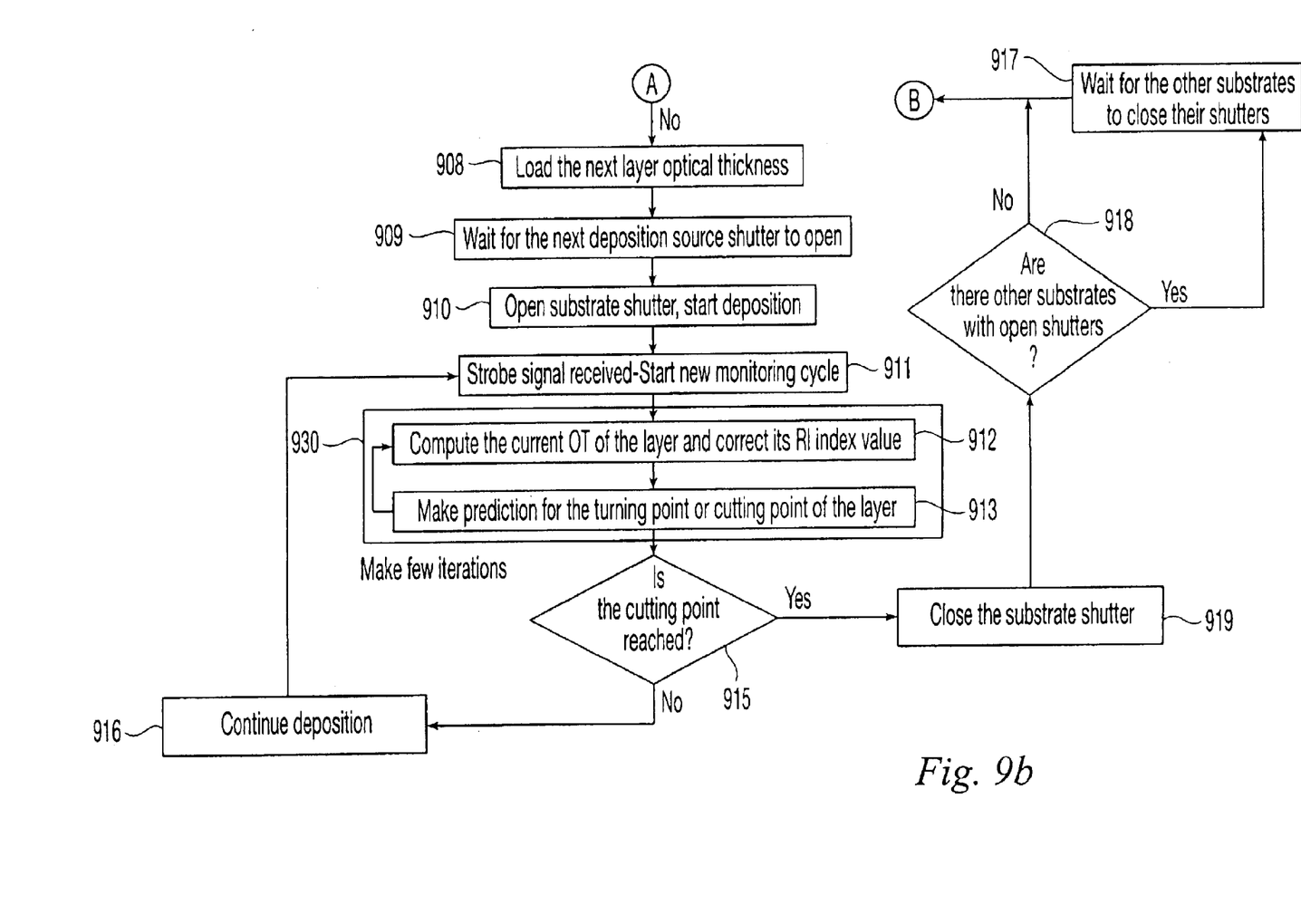

FIG. 9 is a flow diagram of the functionality performed by an optical monitoring system in accordance with one embodiment of the present invention when performing the deposition and in-situ monitoring process. In other embodiments, the functionality can be performed by hardware, or any combination of hardware and software. The functionality may be changed to account for a particular vacuum chamber, type of substrate and/or substrate holder, the type and geometry of the monitored substrates, rotation speed and substrate wobbling during the rotation and many other parameters. Embodiments of the functionality differs from machine to machine, substrate to substrate and coating to coating.

Initially, at box 901 input data for the refractive indices of the substrate, all deposited materials and the surrounding medium, the ambient temperature of deposition, the reactive gas flow rates and their partial pressures, the parameters of the deposition sources such as ion current and/or anode-cathode voltage, ramp times, bias voltages, etc. is received by the optical monitoring system. Also input is the rotation speed and the monitoring wavelength and its bandwidth (in case of broadband sources), and the duration of the monitoring pulse for all coatings which are going to be deposited.

At box 902 the coating design formulas are loaded into the optical monitoring system for all monitored substrates, which are generally numbered with respect to one rotation cycle of the substrate holder. For this purpose initial calibration of the "position one" or strobe mark is used.

At box 903 a sequence deposition sources to be used during the whole process is inputted. An example of a sequence is "Substrate/L/H/L/H/M/L . . . ," etc., with L, H and M meaning material with low, high and medium (in some cases metal) refractive index. In other embodiments, the deposition source sequence is determined automatically by a computer from the input coating designs.

At box 904 substrate rotation is started at constant speed. It is important to start the rotation as early in the process as possible in order to leave time for rotation stabilization and to detect as early as possible any malfunctioning in the mechanical and monitoring system set up. In some embodiments, a stroboscopic control of the rotation speed and the monitored substrate wobbling are also used.

At box 905 all the needed deposition sources are started with their own shutters closed and are kept in "ready" position all the time in order not to waste time for their start and preparation during the process and to avoid substrate thermal shocks during the deposition.

At box 906 the optical monitoring system is turned on. The operation of the monitoring system can be checked and calibrated with regard to the transmission/reflection of the bare substrates as they rotate. In some cases the monitoring system can perform this calibration process automatically. Trivial solutions are then checked for (such as no coating formula is loaded or void optical coating is requested).

At decision point 907, it is determined if the design formula is reached, if not, at box 908 the first layer (or the next layer if box 908 has already been executed once) to be deposited is loaded into memory, at box 909 the system waits for the next deposition source shutter to open, and at box 910 the shutter is opened in front of the appropriate deposition source and the layer depositions starts.

As soon as the first strobe signal is received at box 911, the appropriate monitoring device starts the monitoring process and the received digital data is processed. The transmission values received during one monitoring pulse are averaged, and the average value is compared to the target one given by the coating formula. Since during one rotation cycle only a very small amount of material is deposited, the target optical thickness value is far from being reached (since it requires hundreds or thousands of rotation cycles to be made). However, because the deposited material from one or several rotation cycles changes the transmission/reflection value of the substrate-coating system compared to the bare substrate, a new measured value at box 912 provides needed information for calculating the optical thickness of the already deposited film.

Using the calculated value and assuming that the next deposition cycles would have the same duration as the previous, a prediction is made at box 913 as to what would be the transmission value and the optical thickness after the next rotation cycle. The next cycle calculation may confirm the predicted values, but may differ slightly from them. In case of a difference, a new refractive index of the deposited material is calculated and a new prediction for the values which would be measured during the next cycle is made. Before the target optical thickness is reached, an adequate number of iterations is performed to be able to determine with high accuracy the real refractive index of the deposited material and the accurate optical thickness of the deposited layer. The iterative process of calculations is performed in box 930.

During its increase, the monitored film optical thickness due to light interference, creates a periodic transmission (and reflection) function, which is easily monitored on the screen. The point at which the monitored function must cease when the target optical thickness is reached is usually referred to as the "cutting point". After several iterations of optical thickness and refractive index calculations, a reliable prediction can be made when the cutting point must happen. After each rotation cycle it checks whether the cutting point is achieved at decision point 915. If not, the deposition continues at box 916. When the needed optical thickness is achieved, the shutter in front of the substrate is closed at box 919, and the optical monitoring system waits at box 917 until all other shutters are closed and the deposition source is ready to deposit the new layer. The deposition and monitoring ultimately ends at box 920.

As described, an embodiment of the present invention is an optical monitoring system that solves many of the problems of the prior art such as lack of portability and the inability to separately monitor different substrates. Embodiments of the present invention is a portable device that removes the limitations related to the chamber design and geometry. The portability allows the embodiments of the invention to be small and easy to install and uninstall in vacuum chambers having different geometries, including old and custom designed chambers. Further, embodiments of the invention can be installed at different locations in the same chamber, and more than one monitoring systems can be installed in the same vacuum chamber and, therefore, more than one substrate or specimen can be monitored during one deposition process at the same or at different wavelengths.

The portability features, combined with the feature of autonomous mechanical shutters, is very beneficial when the size of the needed thin film filters is small, but the coating is sophisticated and/or needs to be done at many different center wavelengths, as is the case with DWDM narrow bandpass filters or color separation filters. Embodiments of the present invention allow during one deposition process different areas of the same large substrate to be monitored separately and independently one from another at the same or at different wavelengths, which allows larger number of quality filters or filters at different center wavelengths to be obtained after dicing a large coated substrate.

Further, with embodiments of the present invention more than one optical coating formula can be run on different monitored substrates during one process. This is useful when a small number of deposited optical filters is needed, but when many similar (but different) types of filters are needed. Most coating production processes typically require only two materials to be changed in alternating manner—one with a high and one with a low index of refraction. In such a process, the optical thickness of the individual layers becomes the only variable from formula to formula allowing a vast variety of spectral shapes and types of filters to be designed. Therefore, it is very beneficial to deposit different coating formulas at the same time on different substrates as the sequence of deposited materials is always the same. However, even when more than two deposition materials are needed for some special filters, this does not limit the described functionality of embodiments of the present invention.

Examples of filters that can be successfully deposited during one process include filters for research and development, prototype development, gain flattening filters for EDFA, different anti-counterfeiting filters, some medical or surveillance filters, etc. The ability to run several different filters on different substrates or different areas of the same substrate during one process cannot be done with known prior art. However, such function is very important for better coating equipment utilization and R&D/prototype expense and time-to-market reduction.

Further, with appropriate wavelength switching or multiplexing and electronic and software control it is possible to monitor with the same monitoring device independently more than one substrate on a holder at different wavelengths or more than one area of the same substrate with embodiments of the present invention.

With embodiments of the present invention, instead or running an optical beam through the vacuum chamber, the optical path of the monitoring light beam is much smaller, allowing only the monitored substrate to cross it. Therefore, the optical path is comparable to the thickness of the monitored specimen or smaller.

Embodiments of the optical monitoring system of the present invention do not require light input and output windows, an optically clear path between those windows, or constraints to the chamber design or the deposition process. It can also be installed in different types of existing or custom designed vacuum chambers which are not originally designed for having optical monitoring. Both input and output light ports are found at the same thermal, pressure and light conditions, which reduces significantly the sources of errors during the monitoring process. In addition, because embodiments can be easily changed, or swapped in and out of the chamber, embodiments of the present invention can be made disposable and be intended to be replaced when they are worn out or dirty.

Several embodiments of the present invention are specifically illustrated and/or described herein. However, it will be appreciated that modifications and variations of the present invention are covered by the above teachings and within the purview of the appended claims without departing from the spirit and intended scope of the invention.

What is claimed is:

1. An optical monitoring system for monitoring thin film deposition on a substrate, said system comprising:

a support configured to be attached on an inside of a deposition chamber;

a first fiber optic collimator supported by said support;

a first fiber for incoming light coupled to said first fiber optic collimator; and a second fiber for outgoing light optically coupled to said first fiber optic collimator;

wherein said first fiber optic collimator comprises a two-fiber fertule that is coupled to said first fiber and said second fiber, wherein said second fiber transmits reflected light.

2. An optical monitoring system for monitoring thin film deposition on a substrate, said system comprising:

a support configured to be attached on an inside of a deposition chamber;

a first fiber optic collimator supported by said support;

a first fiber for incoming light coupled to said first fiber optic collimator;

a second fiber for outgoing light optically coupled to said first fiber optic collimator; and a second fiber optic collimator coupled to said second fiber, wherein said second fiber transmits transmitted light.

3. An optical monitoring system for monitoring thin film deposition on a substrate, said system comprising:

a support configured to be attached on an inside of a deposition chamber;

a first fiber optic collimator supported by said support;

a first fiber for incoming light coupled to said first fiber optic collimator;

a second fiber for outgoing light optically coupled to said first fiber optic collimator; and a second fiber optic collimator coupled to said second fiber, wherein said second fiber transmits reflected light.

4. An optical monitoring system for monitoring thin film deposition on a substrate, said system comprising:

a support configured to be attached on an inside of a deposition chamber;

a first fiber optic collimator supported by said support;

a first fiber for incoming light coupled to said first fiber optic collimator; and a second fiber for outgoing light optically coupled to said first fiber optic collimator;

wherein said first fiber optic collimator comprises a GRIN lens.

5. The optical monitoring system of claim 4, wherein said first fiber optic collimator comprises a tap optical filter and an alignment glass rod.

6. An optical monitoring system for monitoring thin film deposition on a substrate, said system comprising:

a support configured to be attached on an inside of a deposition chamber;

a first fiber optic collimator supported by said support;

a first fiber for incoming light coupled to said first fiber optic collimator; and a second fiber for outgoing light optically coupled to said first fiber optic collimator;

wherein the substrate comprises a monitored area, that is monitored by collimated light from said first fiber optic collimator.

7. An optical monitoring system for monitoring thin film deposition on a substrate, said system comprising:

a support configured to be attached on an inside of a deposition chamber;

a first fiber optic collimator supported by said support;

a first fiber for incoming light coupled to said first fiber optic collimator;

a second fiber for outgoing light optically coupled to said first fiber optic collimator; and a strobe signal generator.

8. An optical monitoring system for monitoring thin film deposition on a substrate, said system comprising:

a support configured to be attached on an inside of a deposition chamber;

a first fiber optic collimator supported by said support;

a first fiber for incoming light coupled to said first fiber optic collimator;

a second fiber for outgoing light optically coupled to said first fiber optic collimator;

a substrate holder configured to hold the substrate; a first shutter that prevents incoming deposition material from contacting at least a first portion of the substrate; and a second shutter that prevents incoming deposition material from contacting at least a second portion of the substrate.

9. An optical monitoring system for monitoring thin film deposition on a substrate, said system comprising:

a support configured to be attached on an inside of a deposition chamber;

a first fiber optic collimator supported by said support;

a first fiber for incoming light coupled to said first fiber optic collimator;

a second fiber for outgoing light optically coupled to said first fiber optic collimator;

a substrate holder configured to hold the substrate; and a first shutter that prevents incoming deposition material from contacting at least a first portion of the substrate;

wherein said first shutter is closed when a predetermined optical thickness on the substrate is reached.

10. The optical monitoring system of claim 9, wherein a determination is made that a predetermined optical thickness on the substrate is reached using an iterative process that includes a calculation of a predicted optical thickness.

11. An optical monitoring system for monitoring thin film deposition on a substrate, said system comprising:

a support configured to be attached on an inside of a deposition chamber;

a first fiber optic collimator supported by said supports;

a first fiber for incoming light coupled to said first fiber optic collimator; and a second fiber for outgoing light optically coupled to said first fiber optic collimator;

wherein said first fiber and said second fiber are comprised of a single fiber, and further comprising a beam splitter coupled to said single fiber.

12. The optical monitoring system of claim 11, wherein the first fiber is configured to both transmit and reflect light.

13. The optical monitoring system of claim 11, wherein the beam splitter is configured to separate a reflected signal from an incoming signal.

14. The optical monitoring system of claim 11, wherein the beam splitter is an optical circulator.

15. A thin film substrate deposition device comprising:

a deposition chamber, a support coupled to said deposition chamber;

a first fiber optic collimator coupled to said support;

a first fiber for incoming light coupled to said first collimator;

a second fiber for outgoing light optically coupled to said first fiber optic collimator;

a substrate holder coupled to said deposition chamber; and a first shutter coupled to said deposition chamber and movable from an open position to a closed position that prevents incoming deposition material from contacting at least a first portion of the substrate.

16. The thin film substrate deposition device of claim 15, wherein said first fiber optic collimator comprises a two-fiber ferule that is coupled to said first fiber and said second fiber, wherein said second fiber transmits reflected light.

17. The thin film substrate deposition device of claim 15, further comprising:

a second fiber optic collimator coupled to said support, wherein said second fiber transmits transmitted light.

18. The thin film substrate deposition device of claim 15, further comprising:

a second fiber optic collimator coupled to said support, wherein said second fiber transmits reflected light.

19. The thin film substrate deposition device of claim 15, wherein said first fiber optic collimator comprises a GRIN lens.

20. The thin film substrate deposition device of claim 19, wherein said first fiber optic collimator comprises a tap optical filter and alignment glass rod.

21. The thin film substrate deposition device of claim 15, wherein the substrate comprises a monitored area that is monitored by collimated light from said first fiber optic collimator.

22. The thin film substrate deposition device of claim 15, further comprising:

a strobe signal generator.

23. The thin film substrate deposition device of claim 15, further comprising:

a second shutter that prevents incoming deposition material from contacting at least a second portion of the substrate.

24. The thin film substrate deposition device of claim 15, wherein said first shutter is closed when a predetermined optical thickness on the substrate is reached.

25. The thin film substrate deposition device of claim 24, wherein a determination is made that a predetermined optical thickness on the substrate is reached using an iterative process that includes a calculation of a predicted optical thickness.

26. The thin film substrate deposition device of claim 15, wherein said first fiber and said second fiber are comprised of a single fiber, and further comprising a beam splitter coupled to said single fiber.

27. The thin film substrate deposition device of claim 15, further comprising a substrate holder configured to rotate the substrate.

28. The thin film substrate deposition device of claim 27, wherein the substrate is rotated around more than one axis.

29. The thin film substrate deposition device of claim 28, wherein the substrate undergoes planetary rotation.

30. The thin film substrate deposition device of claim 15, wherein the substrate is monitored from its back side.

31. The thin film substrate deposition device of claim 15, wherein the first fiber optics collimator is attached to the substrate.

32. The thin film substrate deposition device of claim 31, wherein the first fiber optics collimator is attached to the substrate by glue.

33. The deposition chamber according to claim 15, wherein the substrate is provided with a strobe mark on a backside thereof for optical monitoring.

34. A deposition chamber having an optical monitoring system therein suitable for monitoring thin film deposition on a substrate, said optical monitoring system comprising:

a first fiber for incoming light coupled to a first fiber optic collimator;

a second fiber for outgoing light optically coupled to said first fiber optic collimator; and a first shutter movable between:

an open position in which said first shutter permits incoming deposition material to contact at least a first portion of a substrate, and a closed position in which said first shutter prevents incoming deposition material from contacting said at least a first portion of a substrate.

35. The deposition chamber according to claim 34, further comprising:

a second shutter configured, when in the closed position, to prevent incoming deposition material from contacting at least a second portion of a substrate.

36. The deposition chamber according to claim 35, wherein the first and second portions belong to separate substrates.

37. The deposition chamber according to claim 35, wherein the first and second abutters are autonomously controlled.

38. The deposition chamber according to claim 37, wherein the first and second abutters are connected to a substrate holder within the deposition chamber.

39. The deposition chamber according to claim 38, wherein the first and second shutters are rotated between the open and closed positions by a driver fixed on the substrate holder.

40. The deposition chamber according to claim 34, wherein said first fiber optic collimator comprises a two-fiber ferule, an alignment glass rod, a tap optical filter and a GRIN lens.

41. The deposition chamber according to claim 40, wherein said two-fiber ferule is coupled to said first and second fibers, and wherein said second fiber transmits reflected light.

42. The deposition chamber according to claim 34, further comprising: a second fiber optic collimator coupled to said second fiber.

43. The deposition chamber according to claim 42, wherein each of said first and second fiber optic collimators comprises a single-fiber ferul and a GRIN lens.

44. The deposition chamber according to claim 42, wherein said second fiber transmits reflected light.

45. The deposition chamber according to claim 42, wherein said second fiber transmits transmitted light.

46. The deposition chamber according to claim 34, wherein said first fiber and said second fiber are comprised of a single fiber, and further comprising a beam splitter coupled to said single fiber.

47. The deposition chamber according to claim 34, wherein said first fiber optic collimator comprises a GRIN lens.

48. The deposition chamber according to claim 34, wherein said first fiber optic collimator comprises a tap optical filter and an alignment glass rod.

49. The deposition chamber according to claim 34, further comprising:

a strobe signal generator.

50. The deposition chamber according to claim 34, wherein said first shutter is closed when a predetermined optical thickness on the substrate is reached.

51. The deposition chamber according to claim 34, wherein a determination is made that a predetermined optical thickness on the substrate is reached using an iterative process that includes a calculation of a predicted optical thickness.

52. The deposition chamber according to claim 34, further comprising a substrate holder configured to rotate the substrate.

53. The deposition chamber according to claim 52, wherein the substrate undergoes rotation around more than one axis.

54. The deposition chamber according to claim 53, wherein the substrate undergoes planetary rotation.

55. The deposition chamber according to claim 34, wherein the substrate is monitored from its back side.

56. The deposition chamber according to claim 34, wherein the first fiber optic collimator is attached to the substrate.

57. The deposition chamber according to claim 56, wherein the first fiber optic collimator is attached to the substrate by glue.

58. The deposition chamber according to claim 34, wherein the substrate is provided with a strobe mark on a backside thereof for optical monitoring.

* * * * *